United States Patent [19]
Huttner et al.

[11] Patent Number: 5,892,238
[45] Date of Patent: *Apr. 6, 1999

[54] RADIATION THERAPY SHIELDING ASSEMBLY

[75] Inventors: James J. Huttner, Sylvania, Ohio; Andrew J. Milligan, Berwyn, Pa.

[73] Assignee: Bionix Development Corp., Toledo, Ohio

[ * ] Notice: This patent issued on a continued prosecution application filed under 37 CFR 1.53(d), and is subject to the twenty year patent term provisions of 35 U.S.C. 154(a)(2).

[21] Appl. No.: 850,585

[22] Filed: May 2, 1997

[51] Int. Cl.⁶ .................................................. G21F 3/00
[52] U.S. Cl. ................................... 250/515.1; 250/505.1
[58] Field of Search ............................. 250/515.1, 505.1

[56] References Cited

U.S. PATENT DOCUMENTS

| | | |
|---|---|---|
| 1,574,884 | 3/1926 | Hendricks ............................ 250/515.1 |
| 3,539,813 | 11/1970 | Resnick . |
| 4,754,147 | 6/1988 | Maughan et al. .................... 250/505.1 |
| 4,798,961 | 1/1989 | Augustsson . |
| 5,115,139 | 5/1992 | Cotter . |
| 5,160,847 | 11/1992 | Leavitt et al. . |
| 5,166,531 | 11/1992 | Huntzinger . |
| 5,190,990 | 3/1993 | Eichmiller . |
| 5,233,990 | 8/1993 | Barnea . |
| 5,267,294 | 11/1993 | Kuroda et al. . |
| 5,291,404 | 3/1994 | Kurokawa et al. . |
| 5,360,666 | 11/1994 | Eichmiller . |

*Primary Examiner*—Jack I. Berman
*Attorney, Agent, or Firm*—Emch, Schaffer, Schaub & Porcello Co., L.P.A.

[57] ABSTRACT

A radiation therapy shielding assembly is disclosed. The shielding assembly includes a pair of shielding sections. The shielding sections define a cavity for receiving a patient. Each of the shielding sections define a predetermined edge surface. The predetermined edge surfaces of the pair of shielding sections are spaced from one another to define a patient treatment area.

7 Claims, 3 Drawing Sheets

RADIATION THERAPY SHIELDING ASSEMBLY

BACKGROUND

The present invention is directed to an improved shielding assembly for radiation therapy. The present invention provides a shield at the location of the patient which targets the correct area of the patient for proper radiation.

The prior art generally uses a collimator together with shields or deflectors adjacent the radiation beam generator to adjust the radiation beam and direct the desired beam to the target area of the patient.

SUMMARY

The present invention is an improved radiation therapy shielding assembly which is mounted adjacent the patient.

The shielding assembly includes at least two arcuate shielding sections. Each of the sections has a predetermined edge surface. The edge surfaces of the shielding sections are spaced from one another to define a predetermined treatment area on the patient. The radiation beam is directed to such treatment area. The arcuate shielding sections intercept radiation which is outside the predetermined patient target area.

DRAWINGS

DESCRIPTION OF THE PREFERRED EMBODIMENTS

Figure 1:
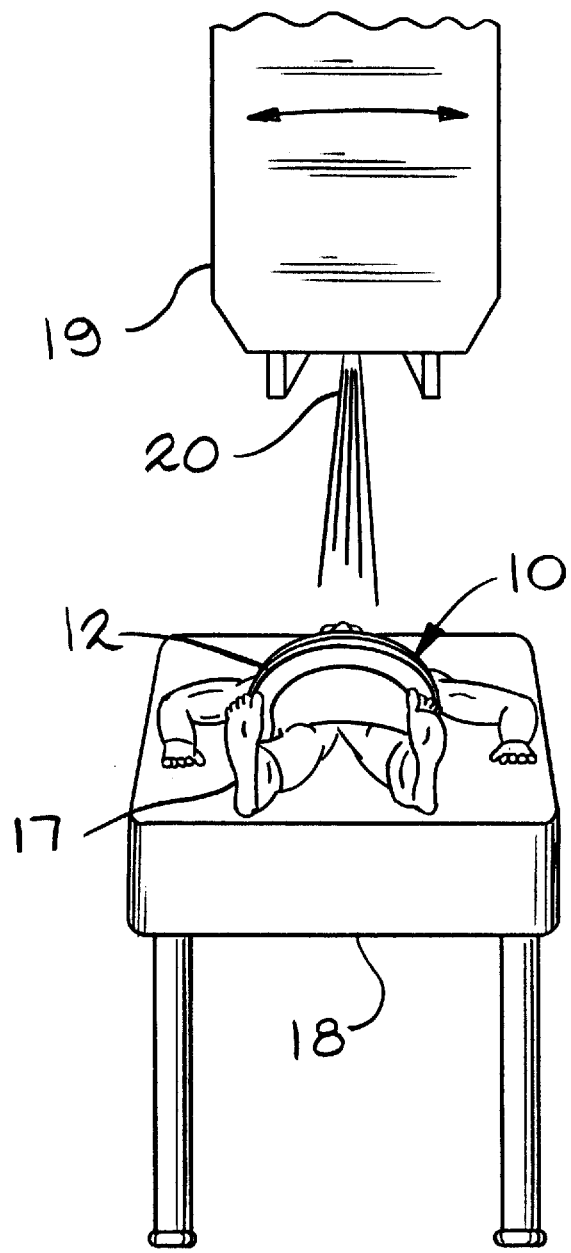
FIG. 1 is a fragmentary perspective view showing a patient positioned beneath a ray generating mechanism and a radiation therapy shielding assembly, according to the present invention, positioned adjacent the patient.

A radiation therapy shielding assembly, according to the present invention is generally indicated by the reference number 10 in FIG. 1.

The shielding assembly 10 includes at least a pair of shielding sections. In the FIG. 1 embodiment, the shielding assembly 10 includes first and second generally arcuate shielding sections 11 and 12. Each of the shielding sections 11 and 12 has a predetermined edge surface 13 and 14. The edge surfaces 13 and 14 are spaced from one another to define a predetermined treatment area 15.

The shielding sections are preferably constructed of a radiation beam blocking material, for example, a lead composition.

Referring to FIG. 1, a patient 17 is positioned on a table 18. The shielding assembly 10 is positioned over the patient 17. A radiation beam mechanism is mounted on a gantry (not shown). The mechanism includes a moving radiation beam head 19 which includes a collimator and moves in the direction of the arrows indicated in FIG. 1.

The head 19 emits a narrow beam 20. The beam 20 is shaped and is directed to the target area or predetermined treatment area 15 shown in FIG. 2. The beam 20 is adjusted by the use of the collimator. The first shielding section 11 and the second shielding section 12 define patient receiving cavities 22 and 23.

Figure 2:
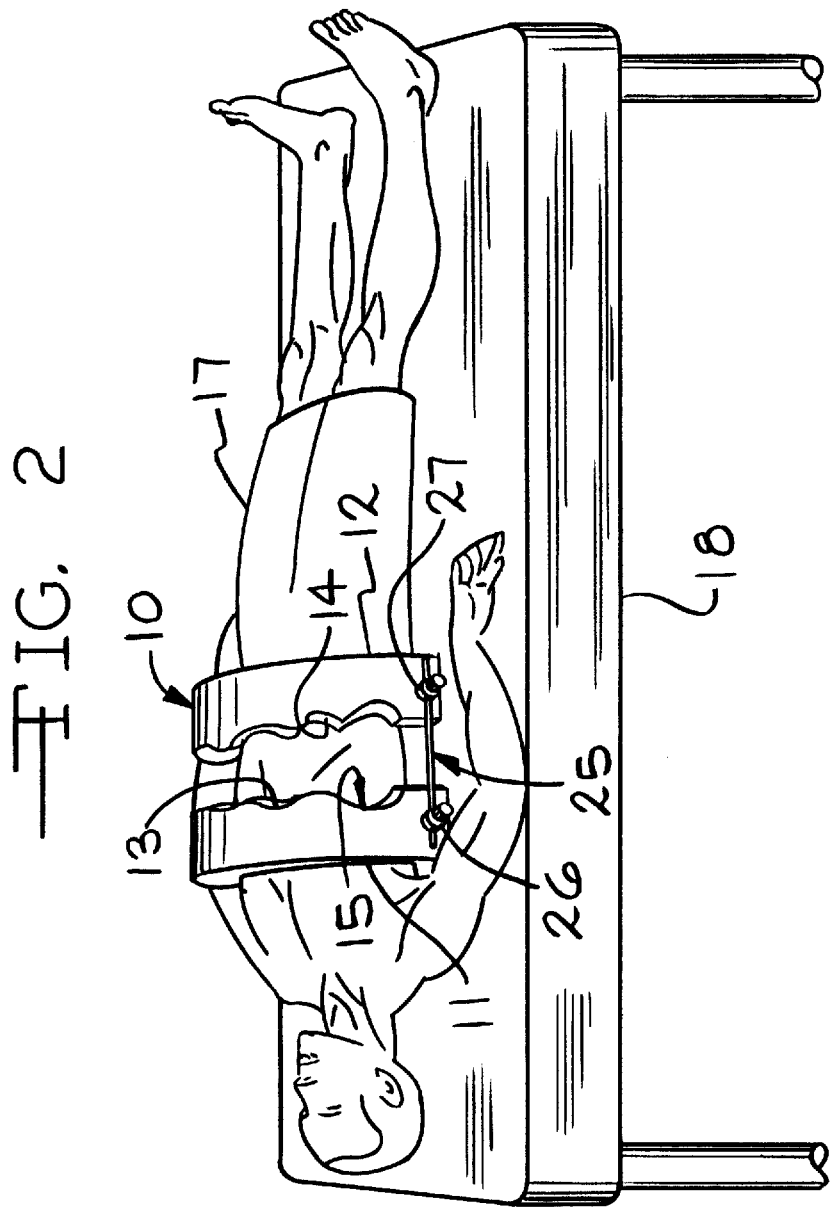
FIG. 2 is an enlarged perspective view showing the shielding assembly, according to the present invention, adjacent the patient.
Figure 3:
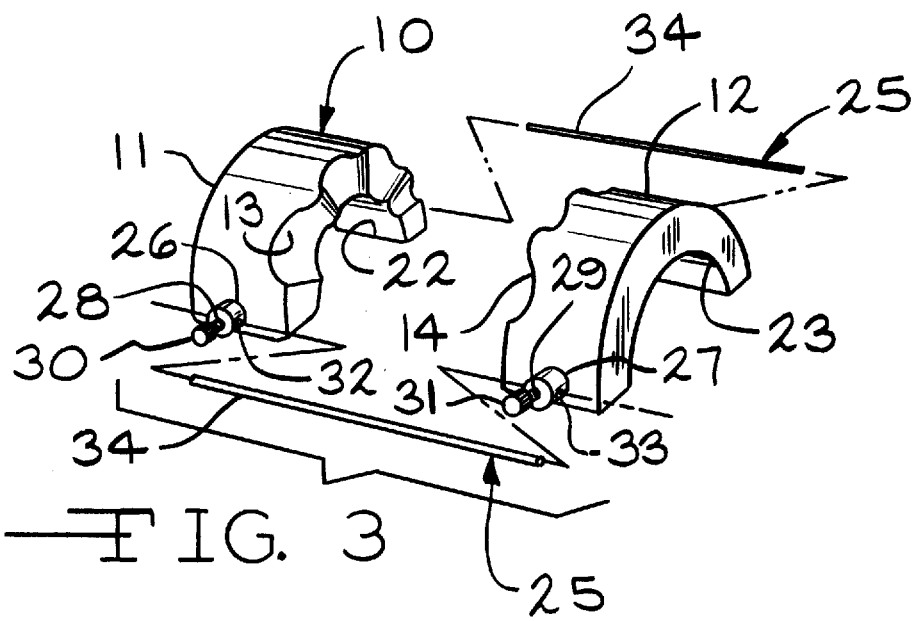
FIG. 3 is an exploded view of the shielding assembly shown in FIG. 2.

In a preferred embodiment, the radiation therapy shielding assembly 10 includes at least one attachment arm extending between said first and second generally arcuate shielding sections 11 and 12. Referring to FIGS. 2 and 3, a pair of attachment arms 25 extend between the shielding sections 11 and 12. Each of the arms 25 includes a pair of sockets 26 and 27 which define threaded center holes 28 and 29, which receive threaded holding screws 30 and 31. Cross holes 32 and 33 extend through the sockets 26 and 27 intersecting the respective center holes 28 and 29.

A rod 34 is slidably mounted in the cross holes 32 and 33. When the end surfaces 13 and 14 are correctly positioned, the holding screws 30 and 31 are rotated until they engage the rod 34 to hold the first and second shielding sections 11 and 12 in correct alignment. The attachment arms 25 are longitudinally adjustable by releasing and re-engaging the holding screws 30 and 31 to adjust the spacing between said first and second generally arcuate shielding sections 11 and 12.

Figure 4:
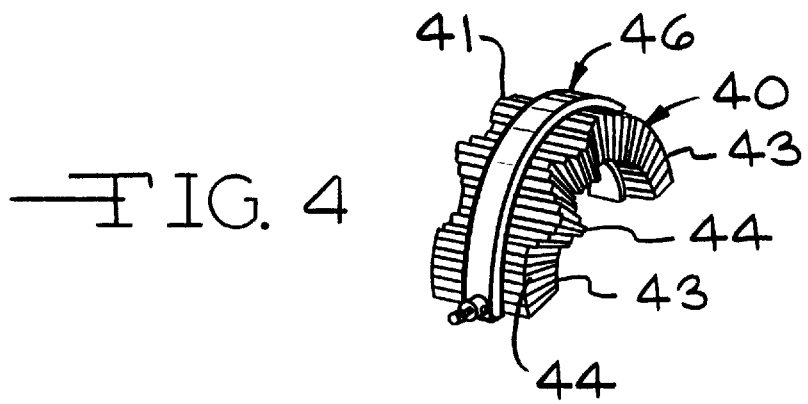
FIG. 4 is a perspective view of another embodiment of an arcuate shielding section, according to the present invention.
Figure 5:
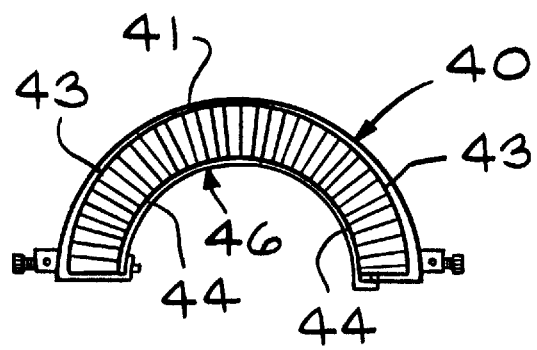
FIG. 5 is an end view, taken on an enlarged scale of the arcuate shielding section, shown in FIG. 4.

Another embodiment of a radiation therapy shielding assembly is indicating by the reference number 40 in FIGS. 4 and 5. The shield assembly 40 includes a pair of shielding sections 41. Each of the first and second shielding sections 41 are constructed in the same manner. Each shielding section 41 includes a plurality of adjacent shielding elements 43. The plurality of shielding elements 43 have a generally truncated cross section being wider at their tops. The shielding elements 43 are longitudinally movable with respect to one another. Each of the shielding elements 43 define an element surface 44.

The plurality of units or element surfaces 44 define the predetermined edge surface 45. The predetermined edge surfaces of the spaced shielding sections 41 define the patient target area, similar to the FIG. 2 embodiment. The shielding elements 43 are preferably constructed of a lead composition and are held in place, relative to one another by a holder assembly 46. The remaining components of the shield assembly 40 are similar to those of the shielding assembly 10.

Many revisions may be made to the above described embodiments without departing from the scope of the present invention or from the following claims.

We claim:

1. A radiation therapy shielding assembly for positioning closely adjacent a patient to be treated, said shield assembly being designed to be used with a radiation beam mechanism that produces a radiation beam for treating a patient, said radiation beam mechanism being designed to move relative to said shield assembly, said radiation therapy shielding assembly comprising first and second generally arcuate shielding sections, each of such sections having a contoured predetermined edge surface, said edge surface of said first and second shielding sections being spaced from one another to define a variable predetermined treatment area adjacent the patient whereby the edge surfaces of said first and second shielding sections control the shape of said radiation beam that contacts said patient as said radiation beam mechanism moves relative to said shielding assembly.

2. A radiation therapy shielding assembly, according to claim 1, wherein said arcuate shielding sections define a patient receiving cavity.

3. A radiation therapy shielding assembly, according to claim 1, wherein said arcuate shielding sections are formed from a lead composition.

4. A radiation therapy shielding apparatus, according to claim 1, including an attachment arm extending between said first and second generally arcuate shielding sections.

5. A radiation therapy shielding apparatus, according to claim 4, wherein said attachment arm is longitudinally adjustable to adjust the spacing between said first and second generally arcuate shielding sections.

6. A radiation therapy shielding apparatus, according to claim 1, wherein each of said first and second generally arcuate shielding sections comprise a plurality of adjacent shielding elements, said shielding elements being longitudinally movable with respect to one another, each of said shielding elements defining an element surface which forms a unit of a section edge surface, said plurality of shielding elements defining such predetermined treatment area adjacent the patient.

7. A radiation therapy shielding assembly, according to claim 6, including a holder assembly retaining said plurality of shielding elements into an adjacent relationship whereby a plurality of element surfaces defined by said plurality of shielding elements define said predetermined edge surface.

* * * * *